United States Patent [19]
Gettig et al.

[11] Patent Number: 5,609,584
[45] Date of Patent: Mar. 11, 1997

[54] ADAPTOR SYSTEM FOR USE WITH A SYRINGE

[75] Inventors: William A. Gettig; Larry E. Shook, both of Millheim, Pa.

[73] Assignee: Gettig Technologies, Inc., Spring Mills, Pa.

[21] Appl. No.: 481,080

[22] Filed: Jun. 7, 1995

Related U.S. Application Data

[63] Continuation-in-part of Ser. No. 246,611, May 18, 1994, abandoned.

[51] Int. Cl.$^6$ ................................................. A61M 25/00
[52] U.S. Cl. ........................................... 604/283; 604/905
[58] Field of Search ................................. 604/283, 905, 604/192, 411–414, 284

[56] References Cited

U.S. PATENT DOCUMENTS

| | | | |
|---|---|---|---|
| Re. 34,045 | 8/1992 | McFarland | 604/198 |
| 1,793,068 | 2/1931 | Dickinson . | |
| 2,574,964 | 11/1951 | Eisnestark | 128/218 |
| 3,640,278 | 2/1972 | Friedman | 128/218 |
| 4,425,120 | 1/1984 | Sampson et al. | 604/198 |
| 4,631,057 | 12/1986 | Mitchell | 604/198 |
| 4,655,751 | 4/1987 | Harbaugh | 604/198 |
| 4,681,567 | 7/1987 | Masters et al. | 604/198 |
| 4,693,708 | 9/1987 | Wanderer et al. | 604/192 |
| 4,702,738 | 10/1987 | Spencer | 604/187 |
| 4,723,943 | 2/1988 | Spencer | 604/198 |
| 4,737,144 | 4/1988 | Choksi | 604/198 |
| 4,738,663 | 4/1988 | Bogan | 604/198 |
| 4,743,233 | 5/1988 | Schneider | 604/192 |
| 4,801,295 | 1/1989 | Spencer | 604/198 |
| 4,804,372 | 2/1989 | Laico et al. | 604/198 |
| 4,816,022 | 3/1989 | Poncy | 604/198 |
| 4,846,796 | 7/1989 | Carrell et al. | 604/110 |
| 4,850,994 | 7/1989 | Zerbst et al. | 604/198 |
| 4,874,383 | 10/1989 | McNaughton | 604/198 |
| 4,892,521 | 1/1990 | Laico et al. | 604/192 |
| 4,894,055 | 1/1990 | Sudnak | 604/198 |
| 4,897,083 | 1/1990 | Martell | 604/192 |
| 4,898,590 | 2/1990 | Andors | 604/198 |
| 4,915,701 | 4/1990 | Halkyard | 604/198 |
| 4,923,447 | 5/1990 | Morgan | 604/198 |
| 4,927,417 | 5/1990 | Moncada et al. | 604/198 |
| 4,935,010 | 6/1990 | Cox et al. | 604/122 |
| 4,935,016 | 6/1990 | Deleo | 604/198 |
| 4,998,924 | 3/1991 | Ranford | 604/798 |
| 5,019,051 | 5/1991 | Hake | 604/198 |
| 5,026,354 | 6/1991 | Kocses | 604/195 |
| 5,137,521 | 8/1992 | Wilkins | 604/198 |
| 5,160,326 | 11/1992 | Talonn et al. | 604/198 |
| 5,197,953 | 3/1993 | Colonna et al. | 604/110 |
| 5,201,717 | 4/1993 | Wyatt et al. | 604/192 |
| 5,250,037 | 10/1993 | Bitdinger | 604/192 |
| 5,254,100 | 10/1993 | Huband | 604/198 |
| 5,324,272 | 6/1994 | Smedley et al. | 604/193 |
| 5,356,396 | 10/1994 | Wyatt et al. | 604/283 |

FOREIGN PATENT DOCUMENTS

| | | |
|---|---|---|
| 706714 | 6/1931 | France . |
| 130863 | 5/1902 | Germany . |
| 2225723 | 6/1990 | United Kingdom . |

*Primary Examiner*—John D. Yasko
*Attorney, Agent, or Firm*—Kirkpatrick & Lockhart LLP

[57] ABSTRACT

An adaptor system for a syringe that has a fluid carrying body. In a preferred embodiment, the adaptor system comprises a syringe fitting that has a hollow element protruding therefrom and is attachable to the syringe such that the hollow element is in fluid communication with the fluid carrying body. The system also includes an adaptor member that has a port adapted to receive the hollow element of the syringe fitting in fluid-tight engagement. The adaptor member is provided with at least one protrusion that is adapted to be received in a corresponding T-shaped slot formed in the syringe fitting. When the protrusions are aligned with their corresponding T-shaped slot, the hollow element may be axially inserted into the adaptor port to establish the fluid-tight seal and be selectively rotated in two radial directions relative to the syringe fitting while maintaining a fluid-tight seal therebetween.

15 Claims, 8 Drawing Sheets

ADAPTOR SYSTEM FOR USE WITH A SYRINGE

This is a continuation-in-part of U.S. patent application Ser. No. 08/246,611 filed on May 18, 1994 now abandoned.

BACKGROUND OF THE INVENTION

1. Field of the Invention

This invention relates generally to medical devices and more particularly, to an improved adaptor connector system enabling popular, existing syringes to selectively interface with various intravenous ("I.V.") ports and/or to function as a hypodermic syringe for injecting medicaments subcutaneously.

2. Description of the Invention Background

To enable the most efficient administration of small doses of precise measured amounts of medicament to a patient who has been prepped with an I.V. port, hypodermic syringes have been equipped with special fittings on the front of the syringe barrel. These fittings provide a nose portion constructed to present a close fit within many of the port fittings now being employed, such that, upon manipulation of an attached syringe plunger, medicament is supplied in a controllable manner to the I.V. system through the fitting and into the port. Unfortunately, many I.V. ports being used throughout a sizable number of medical facilities present a configuration that is incompatible with one or more of the popular syringe fittings on the market. Accordingly, a need will be seen for some manner of using existing syringe fittings with a greater number of available I.V. ports and the present adaptor which engages slots in a syringe fitting is felt to solve a long standing problem in this art.

The broad concept of syringe fittings employing attachment devices comprising cooperating slotted formations and wherein attachment and removal of the fitting is accomplished through a twisting action between the components, will be found in U.S. Pat. No. 1,793,068, issued Feb. 17, 1931 to Dickinson; U.S. Pat. No. 2,574,964, issued Nov. 13, 1951 to Eisenstark; and U.S. Pat. No. 5,250,037, issued Oct. 5, 1993 to Bitdinger. Further examples of a twist lock construction to affix a cannula hub to a syringe barrel nose will be found in French Patent No. 706.714 of Jun. 29, 1931 and German Patent No. 130,863 of May 15, 1902.

When equipped with hypodermic needles, syringes are also used to inject precise amounts of medicament subcutaneously. Thus, adaptor systems of the type disclosed in U.S. Pat. No. 4,927,417, issued on May 22, 1990 to Moncada et al. have been developed for attaching hypodermic needles to syringes. Also, in recognition of the risks associated with inadvertent "needle sticks" by the administering medical personnel, various displaceable needle sheaths have been developed. For example, a variety of different needle sheath and guard arrangements are disclosed in U.S. Pat. No. 4,850,994, issued Jul. 25, 1989 to Zerbst et al; U.S. Pat. No. 5,026,354 issued Jun. 25, 1991 to Kocses; U.S. Pat. No. 5,045,066 issued Sep. 3, 1991 to Scheuble et al; U.S. Pat. No. 5,160,326 issued Nov. 3, 1992 to Talonn et al; and U.S. Pat. No. 5,254,100 issued Oct. 19, 1993 to Huband. However, those guard and sheath arrangements are ill-suited for use in connection with a syringe that is equipped to alternatively employ fittings adapted for use in various port arrangements.

As can be gleaned from the above-discussed shortcomings of other syringe arrangements, it is apparent that there is a need for an adaptor system for use with a syringe that can enable the syringe to interface with a variety of different port configurations.

There is a further need for an adaptor system having the attributes mentioned above that can also have a hypodermic needle, cannula, trocar, etc. selectively attached thereto.

There is yet another need for an adaptor system with the above-mentioned attributes that also employs a protective needle sheath or guard that can be easily manipulated to expose the needle without being separated from the syringe.

It will also be appreciated that when a syringe adaptor is inserted into a ports it sometimes becomes necessary to rotate the adaptor or the port-carrying member to establish a fluid-tight connection therebetween. However, when employing adaptors that are attached to a syringe fitting by a twist-lock arrangement, the adaptor can accidently become detached from the syringe fitting during the insertion of the adaptor into the port. Thus, there is still another need for a syringe adaptor that can be readily attached and detached from a syringe fitting and that will not become accidentally detached from the fitting if it becomes necessary to rotate the adaptor or receiving port during the insertion process.

SUMMARY OF THE INVENTION

In accordance with a preferred embodiment of the present invention, there is provided an adaptor system for use in connection with a syringe having a fluid carrying body. In a preferred form, the adaptor system comprises a syringe fitting that has a hollow element protruding therefrom. The syringe fitting is attachable to a syringe such that the hollow element thereof is in fluid communication with the fluid carrying body of the syringe. The preferred system further comprises an adaptor member that has a port therein that has an interior surface that is configured for fluid-tight engagement with the outer surface of the hollow element. At least one protrusion is formed on the adaptor member and is arranged to be selectively inserted into a corresponding T-shaped slot provided in the fitting. When the protrusions are simultaneously aligned with their corresponding T-shaped slots, the hollow element may be axially inserted into the adaptor port to establish a fluid-tight seal therewith. Such arrangement also permits the adaptor to be rotated in two radial directions relative to the syringe fitting while maintaining a fluid-tight seal therebetween.

Accordingly, one of the objects of the present invention is to provide an adaptor system that enables a syringe to interface with a variety of different port configurations.

Another object of the present invention is to provide an adaptor system for modifying the external configuration of a by syringe fitting in order to accommodate I.V. ports as produced various manufacturers.

A further object of the present invention is to provide an improved I.V. port adaptor having a twist lock interface cooperating with a syringe fitting.

Yet another object of the subject invention is to provide an adaptor that may be easily connected and disconnected to a syringe fitting or the like and that may be rotated in two radial directions relative to the syringe fitting without becoming detached therefrom.

It is another object of the subject invention to provide a needle assembly that may be readily attached to and detached from a syringe.

Still another object of the present invention is to provide a detachable needle assembly that is equipped with a protective sheath member that can be selectively manipulated to expose the needle.

These objects and other details and advantages will become further apparent as the present detailed description of the preferred embodiments of the subjection invention proceeds.

BRIEF DESCRIPTION OF THE DRAWINGS

In the accompanying drawings, there is shown present preferred embodiments of the subject invention wherein like reference numerals are employed to designate like parts and wherein.

DESCRIPTION OF THE PREFERRED EMBODIMENT

Figure 1:
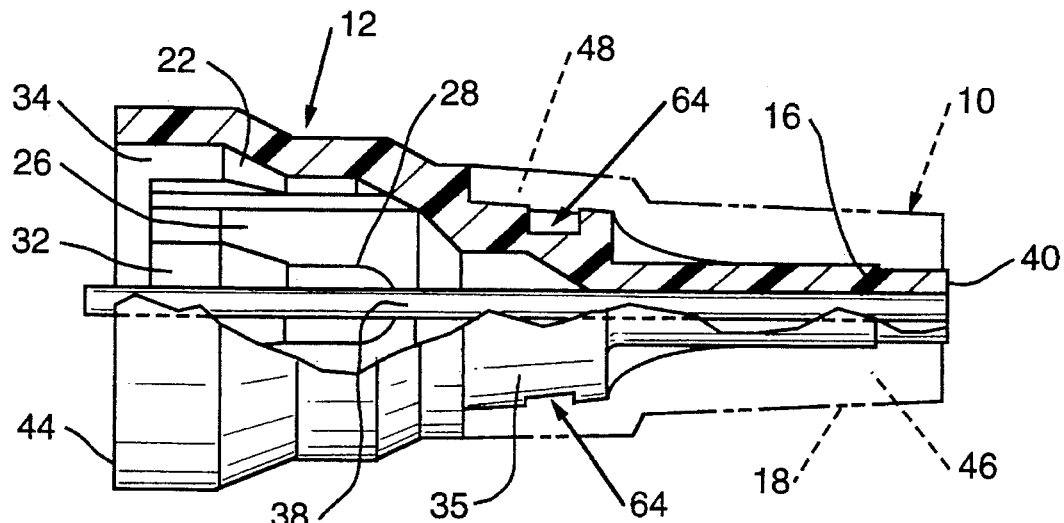
FIG. 1 is a side elevational view, partly in section, of a preferred syringe fitting and illustrates in broken lines a preferred adaptor of the subject invention attached thereto.

Referring now to the drawings for the purposes of illustrating preferred embodiments of the present invention only and not for a purpose of limiting the same, the Figures show an adaptor 10, attachable to a modified syringe fitting 12, in order to permit delivery of the fluid contents of a syringe 14 into the port of an I.V. system (not shown). The profile of the syringe fitting 12 of this invention is similar to that of a popular existing fitting in that the elongated nose 16 is not changed and therefore, a syringe 14 equipped with the fitting 12 may be used with certain available I.V. ports as in the past. However, with the current fitting 12 one may quickly apply an adaptor 10 over the fitting nose 16 when an alternative I.V. port is encountered. In this manner it will be appreciated that an alternately configured tapered side wall 18 is readily available when necessary to achieve compatibility between the syringe fitting 12 and various I.V. ports.

Figure 2:
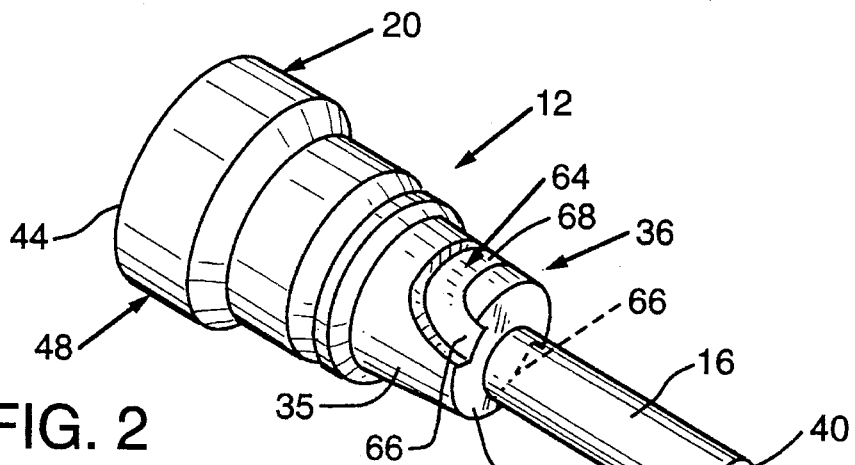
FIG. 2 is a perspective view of the syringe fitting of FIG. 1.
Figure 5:
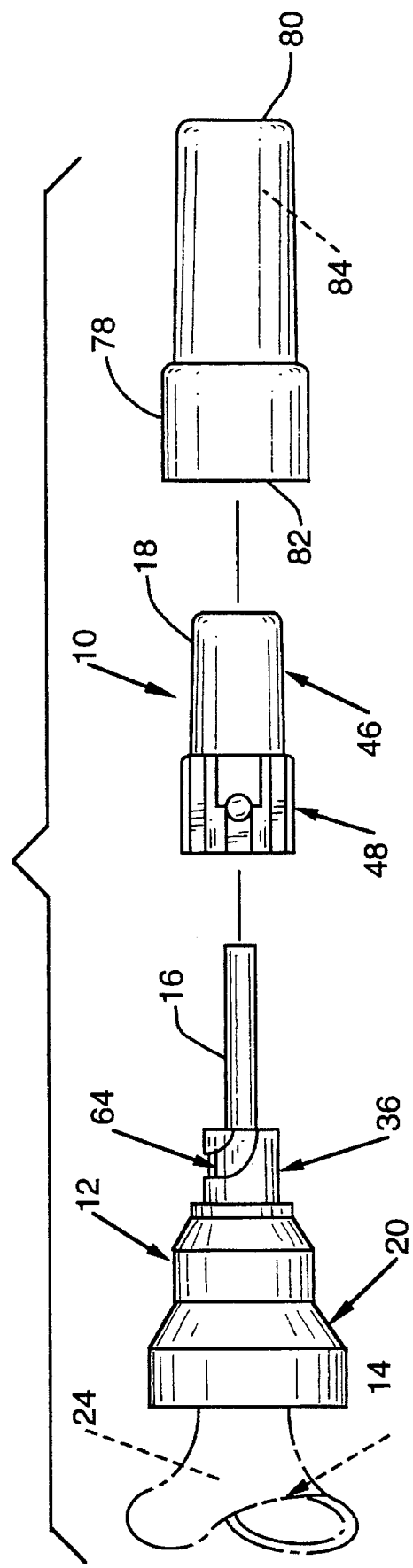
FIG. 5 is an exploded view of a preferred syringe fitting adaptor and protective cover of the subject invention.

To enable the alternative use of either the fitting 12 or adaptor 10, these two components are supplied with mating attachment means that include cooperating elements that facilitate the quick and positive application or removal of the adaptor 10 relative to the syringe fitting 12. As will be seen in FIGS. 1, 2 and 5, the syringe fitting 12 comprises a unitary cylindrical member, preferable of a suitable synthetic resinous product, having an enlarged, rearmost hub 20 with an interior cavity 22. This cavity is adapted to engage and be secured to the forwardmost nose 24 of a syringe 14 constructed of glass or plastics as is well known. To facilitate the assembly and retention of the fitting 12 to the syringe nose 24, the fitting hub includes three webs 26 arranged in a triangular manner within the cavity 22. The passageway 28 within the confines of these webs 26 is configured to provide a close sliding fit with a syringe nose 24 to axially align the center axis of the syringe and its nose opening (not shown), with the longitudinal center axis 30 of the fitting. Relief areas 32 in each web 26 accommodate any interference fit between a syringe nose 24 as it is assembled with the fitting 12 and also assist in maintaining axial alignment as the tapered nose is advanced into the open rear end 34 of the fitting. An appropriate adhesive, as is well known in the art, serves to maintain an assembled fitting 12 affixed to the syringe 14.

When attached as described above, some present conventional fittings may be connected directly to certain I.V. ports on the market. In such cases, the nose 16 enters the I.V. port and is retained as by a luer lock cooperating with the slight taper of the side wall 35 of the fitting mounting section 36. To facilitate compliance with existing protocol, a stainless steel tube 38 may be disposed within the interior of the fitting, extending from the end face 40, through the bore 42 of the nose 16 and past the rear face 44. In this manner, when assembled with a syringe 14, all medicament administered by use of the syringe and its fitting 12 will avoid exposure to any material not already approved by governing authorities, since the tube 38 will be of the same material as a syringe needle.

Figure 3:
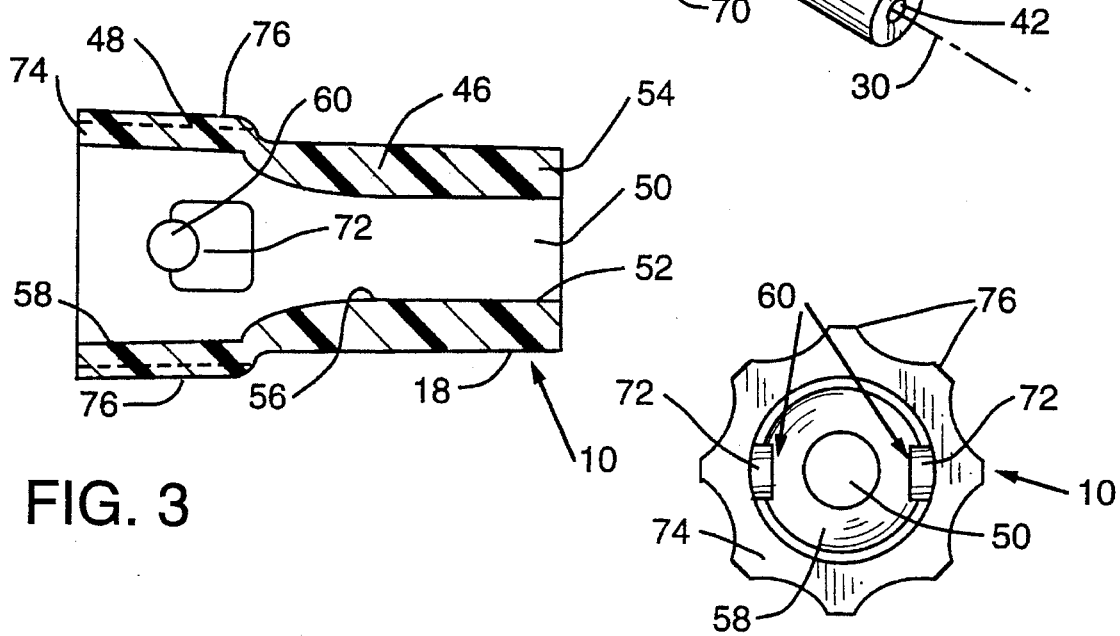
FIG. 3 is a vertical cross-sectional view of the adaptor shown in FIG. 1.
Figure 4:
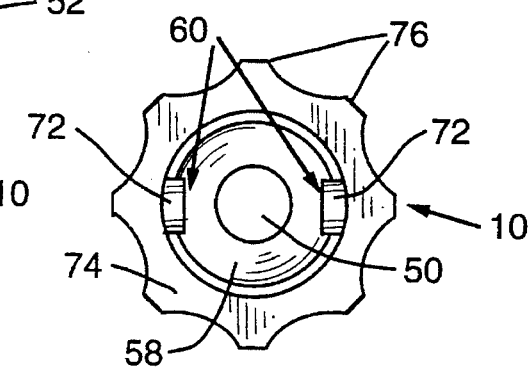
FIG. 4 is a rear elevational view of the adaptor of FIG. 3.

The adaptor 10 of the present invention serves to modify the fitting 12 for accommodation by those I.V. ports designed to accept syringe fittings having a larger diameter than the described fitting nose 16. As will be seen in FIG. 1, with the adaptor 10 affixed to the fitting 12, the slightly tapered side wall 18 of the adaptor presents a significantly altered configuration as compared to that of the fitting nose 16. The construction of the adaptor 10 is shown most clearly in FIGS. 3–5 wherein it will be seen to comprise an elongated nozzle 46 joined to an enlarged rearward skirt 48. The interior cavity or bore 50 presents a forwardmost periphery 52 adjacent the front wall 54, that defines the smallest diameter of the bore and forms a close, sliding fit when assembled about the fitting nose 16. From that point, the inner nozzle wall 56 tapers outwardly and exhibits a substantial increase in diameter as the bore 50 is at its largest diameter, within the adaptor skirt 48. The inner skirt wall 58 likewise is slightly tapered, in conformance with the taper on the fitting side wall 35. These two tapered surfaces are preferably provided with a taper within the range of 1.5 or 2 degrees. However, other taper arrangements may also be successfully used.

To secure the adaptor in place upon the fitting, retention means in the form of a pair of diametrically opposed pins or projections 60—60, are provided within the adaptor bore 50, within the confines of the skirt 48. Preferably, these pins 60 are integral with the remainder of the adaptor and are formed during an injection molding process. To insure a positive retention of the adaptor upon the fitting, sole reliance is not placed upon a wedge fit between the tapered adaptor skirt 48 and tapered side wall 35 of the fitting mounting section 36. As will be seen most clearly in FIG. 2 of the drawings, the fitting mounting section is provided with channel, groove or slot engaging means comprising a pair of diametrically opposite, offset channels 64 each including a front, angular portion 66 communicating with a rear, transverse portion 68. The front, angular channel portions 56 extend through the mounting section front wall 70 and thus provide direct access to the two channels 64 by the pair of pins 60 as the adaptor is moved into assembly relationship with the fitting. The pins 60 are preferably formed with a circular periphery 72 and in any case define a diameter presenting a close sliding fit within the constant width channels 64. With the foregoing arrangements assembly of the adaptor 10 upon the fitting 12 results in the two pins 60 initially entering the two channels 64. As the user applies a clockwise force upon the adaptor, it will simultaneously move rearwardly and be angularly displaced clockwise as the pins are urged rearwardly and to the right, while navigating the front angular portion 66 of the channels. At the time the rear face 74 of the adaptor abuts the shoulder 76 intermediate the hub and mounting sections of the fitting, the two pins 60 will be disposed within the transverse portion of the channels 64, 64 and continued rotary displacement of the adaptor secures a tight fit between the two components, with the end face 40 of the fitting nose 16 projecting ever so slightly beyond the adaptor front wall 54.

When assembled as above described, the enlarged mass of the slightly tapered nozzle 46 presents a configuration capable of mating with a large number of I.V. ports. However, should a user encounter an I.V. port calling for the smaller nose 16 as presented by the fitting 12, one would disregard the adaptor 10 and utilize the fitting 12 itself to engage the I.V. port.

To facilitate the attachment and removal of the adaptor 10, a plurality of longitudinally extending ribs 76 extend from the outer periphery of the skirt 48. In this manner, a user may obtain a positive grip upon the adaptor 10 and readily deliver the necessary rotary movement required to navigate the two pins 60 through the respective channels 64.

To maintain sterility and a seal that is fluid-tight with the adaptor 10, a protective cover 78 is preferably provided. In a preferred embodiment, the protective cover 78 is constructed of a resilient rubber or the like. With one end 80 closed and the other end 82 opening into an interior cavity 84, the adaptor 10 may be completely surrounded, in a close sliding fit within the cover 78. By using a soft pliable rubber composition, the adaptor 10, with the cover attached, may be applied or removed from the fitting 12. This procedure maintains the cleanliness of the adaptor nozzle until actually ready to be attached to an I.V. port while the rubber composition of the cover enhances the grip one's fingers may obtain upon the adaptor's ribs 76.

Figure 6:
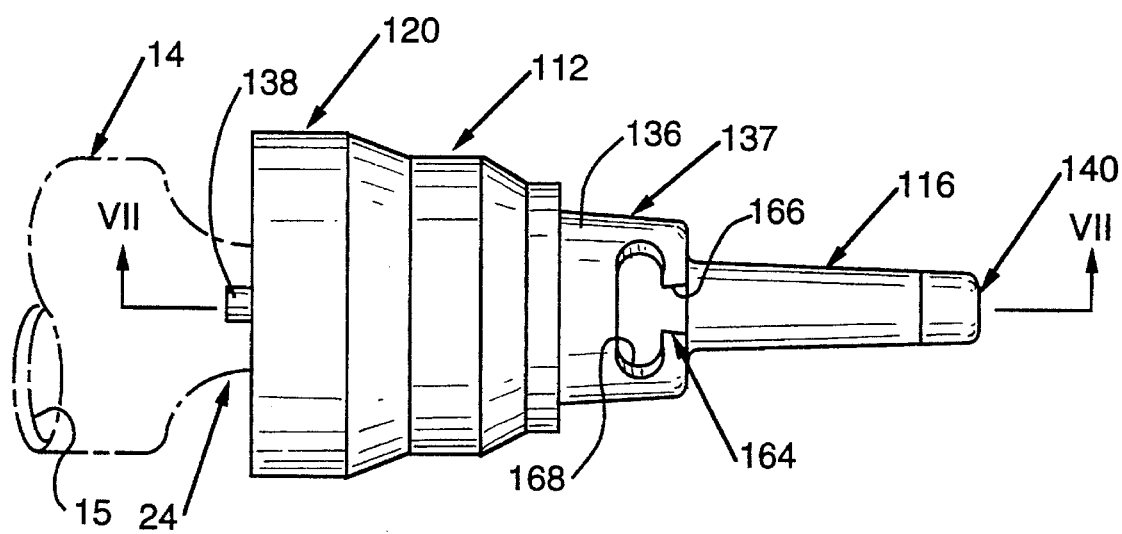
FIG. 6 is a top view of another preferred syringe fitting of the subject invention attached to a syringe having a fluid carrying body.

Another preferred embodiment of the subject invention is depicted in FIGS. 6–9. As can be seen in FIG. 6, a preferred syringe fitting 112 is constructed for attachment to a commercially available syringe 14 that has a fluid carrying or fluid receiving body 15. The skilled artisan will appreciate that the fitting 112 may be used in connection with a variety of different syringe configurations and, thus, the specific syringe construction disclosed herein should not limit the scope of protection afforded to the present invention.

In a preferred embodiment, syringe fitting 112 is preferably fabricated from a resinous material using known fabrication methods. However, those of ordinary skill in the art will readily appreciate that the fitting 112 can be fabricated from other suitable materials without departing from the spirit and scope of the subject invention. As can be seen in FIGS. 6–9, the syringe fitting 112 has a hollow element or nose portion 116 and a hub portion 120. The hub portion 120 preferably has an axial cavity 122 therein that is adapted to receive a nose portion 24 of a syringe 14. To facilitate the assembly and retention of the fitting 112 to the syringe nose 24, the fitting hub 120 includes three webs 126 arranged in a triangular manner within the cavity 122. See FIG. 7. The passageway 128 within the confines of these webs 126 is configured to provide a close sliding fit with a syringe nose 24 to axially align the center axis of the syringe 14 and its nose opening (not shown), with the longitudinal center axis 130 of the fitting. Relief areas 132 in each web 126 accommodate any interference fit between a syringe nose 24 as it is assembled with the fitting 112. The relief areas 132 also assist in maintaining axial alignment of the syringe 14 as the tapered nose 24 is advanced into the open rear end 134 of the fitting 112. An appropriate adhesive, as is well known in the art, preferably serves to affix the syringe 14 to the fitting 112.

Figure 7:
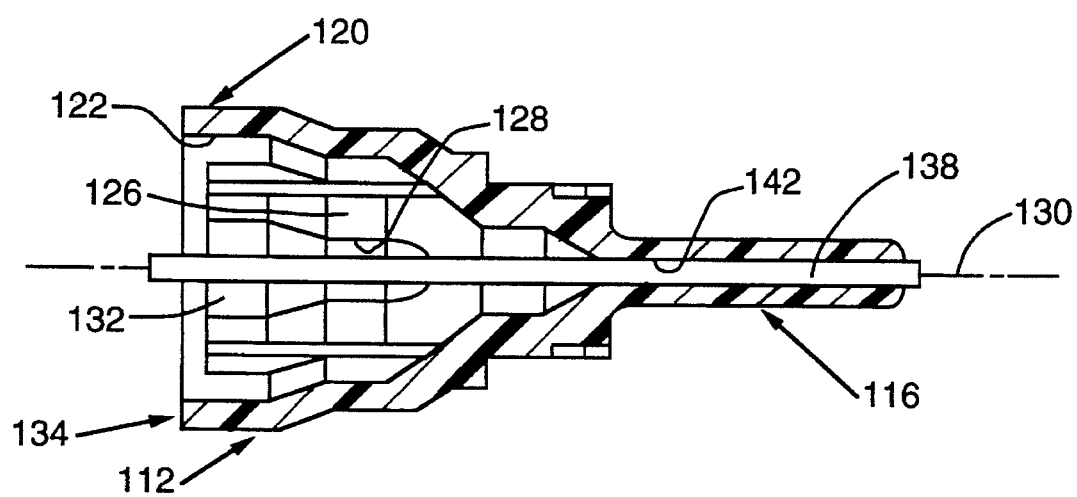
FIG. 7 is a cross-sectional view of the syringe fitting of FIG. 6 taken along line VII—VII in FIG. 6.
Figure 8:
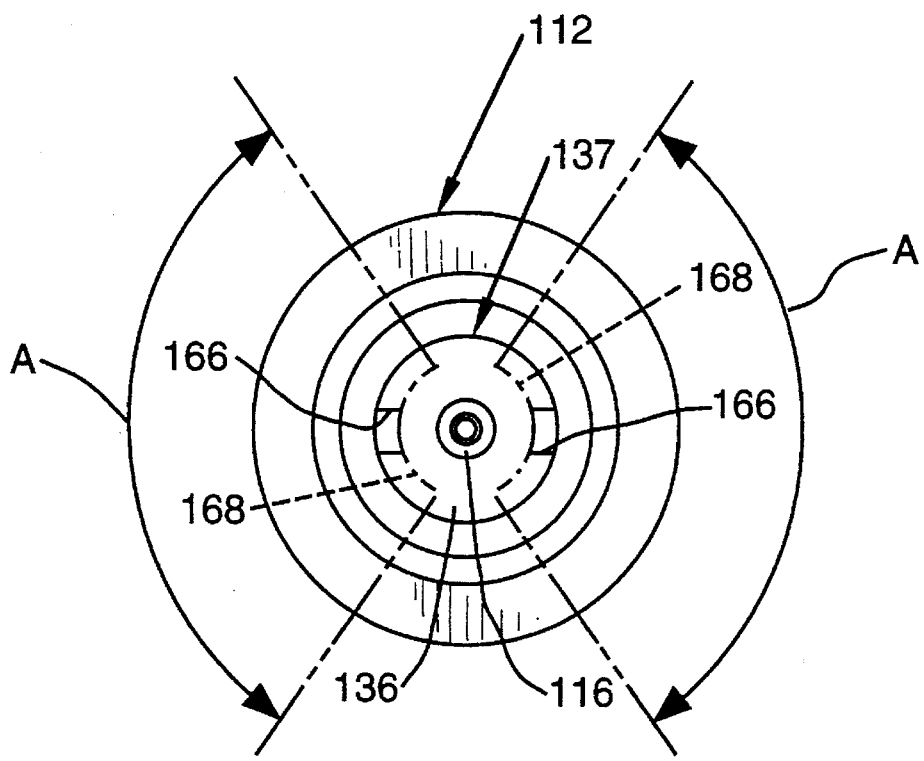
FIG. 8 is an end view of the syringe depicted in FIGS. 6 and 7.
Figure 9:
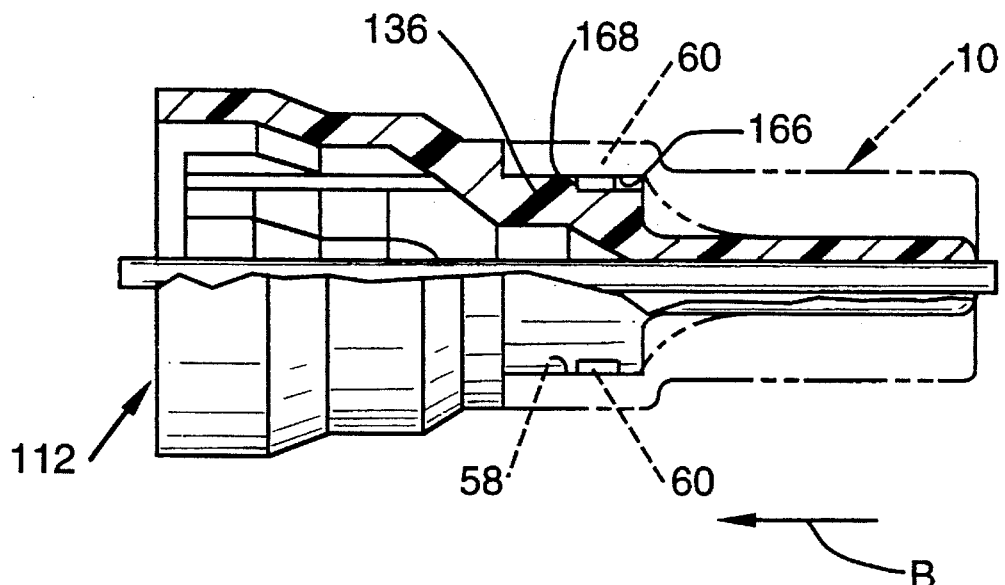
FIG. 9 is a side elevational view, partly in section, of the syringe fitting of FIGS. 6-8 and illustrates in broken lines a preferred adaptor of the subject invention attached thereto.

As can be seen in FIG. 7, a hollow tube 138, preferably fabricated from stainless steel, is preferably disposed within the interior of the fitting 112 and extends from the end face 140, of the nose 116, through a bore 142 in the nose 116 and past the rear face 144 of the hub 120. In this manner, when assembled with a syringe 14, all medicament administered by use of the syringe 14 and the fitting 112 will avoid exposure to any material not already approved by governing authorities.

The fitting 112 is formed with a fitting mounting portion 136 that preferably has a tapered side wall 137 that, as will be discussed in further detail below, is adapted to slidably engage a corresponding tapered interior wall of a port formed in an adaptor to create a fluid-tight seal therebetween. To mechanically secure an adaptor 10 of the type and construction described above, or other member to the fitting 112, two diametrically opposed T-shaped slots 164 are provided in the mounting portion 136. Each slot 164 has an axial portion 166 and a transverse portion 168 that are substantially arranged in the shape of a "T" as shown in FIG. 6. It will be appreciated that the slot portions (166, 168) are sized to slidably receive therein the pins 60 of an adaptor 10 in the manner described above. In a preferred embodiment, the slot portion 168 forms an radially extending pathway on the mounting member 136 of approximately seventy-six degrees (depicted by arrows "A" in FIG. 8). However, the slot portion 168 of a slot 164 may be formed in the outer surface 137 of the mounting portion 136 such that it extends therearound any radial distance and it may even form a continuous passage that extends completely around the circumference of the mounting member 136.

To attach the adaptor 10 of the type described above to the fitting 112, the adaptor 10 is brought into confronting relationship with the fitting 112 such that the pins 60 of the adaptor 10 are axially aligned with a corresponding slot portion 166 in the mounting portion 136 of the fitting 112. The adaptor 10 is then axially displaced on the fitting 112 in the direction depicted by the arrow "B" in FIG. 9 until the pins 60 reach the slot portion 168. Thereafter, the adaptor 10 is rotated in a clockwise or counterclockwise direction relative to the fitting 112 to cause the pins 60 to be advanced to positions in the slot portion 168 such that they are no longer axially aligned with their corresponding slot portions 166 to thereby retain the adaptor 10 on the fitting 112. It will be appreciated that the outer wall 137 of the mounting portion 136 is tapered in conformance with the tapered inner skirt wall 58 of the adaptor 10. Preferably, tapered surfaces (137, 58) are each provided with a taper within the range of 1.5–2.0 degrees. However, other taper arrangements may also be used to establish a fluid-tight seal between the fitting 112 and the adaptor 10. The skilled artisan will readily appreciate that such attachment arrangement permits the adaptor 10 to be rotated in two radial directions relative to the fitting 112 or visa versa without those two members becoming detached from each other and without compromising the fluid-tight seal achieved therebetween. Thus, such arrangement permits the medical personnel inserting the adaptor 10 into a port (not shown) to rotatably manipulate the adaptor 10 without disengaging the adaptor from the fitting 112.

Figure 10:
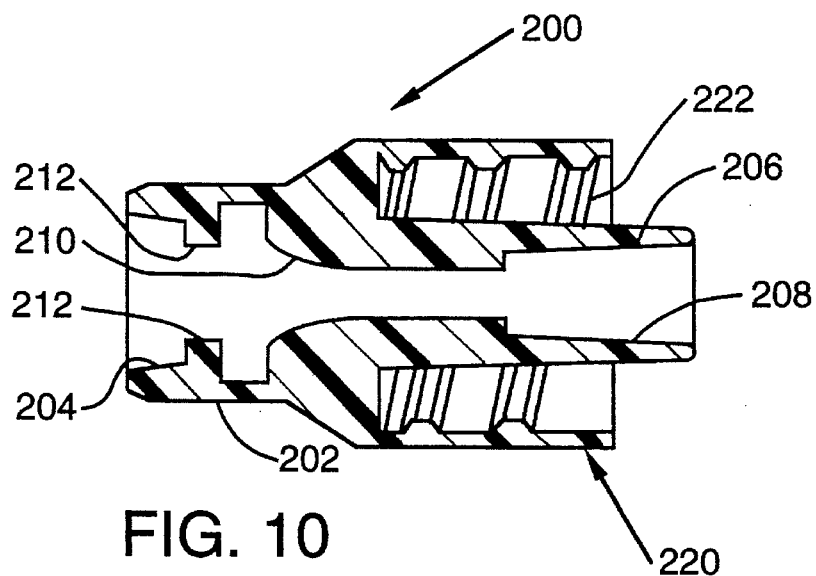
FIG. 10 is cross-sectional view of another preferred adaptor of the present invention.
Figure 11:
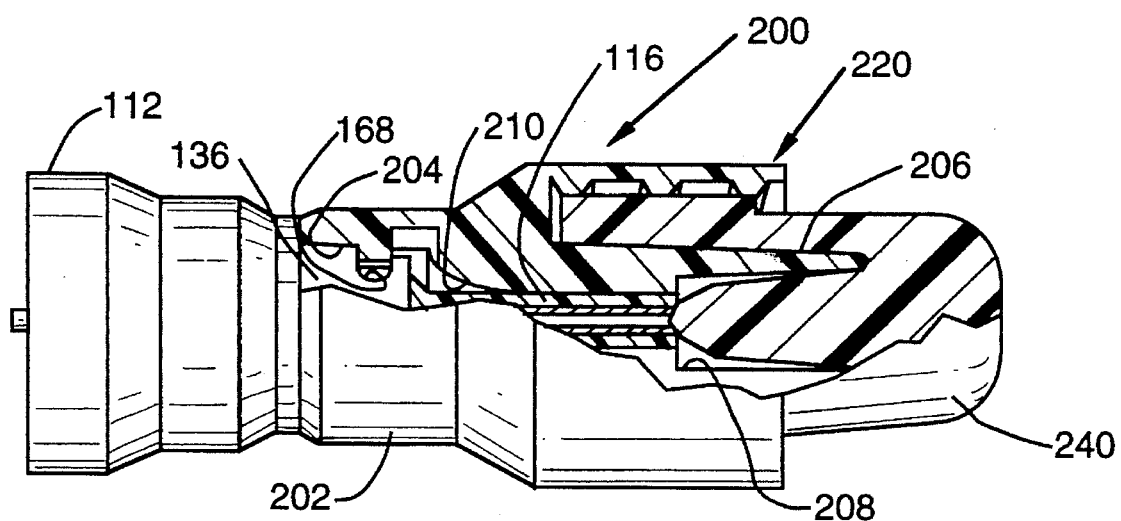
FIG. 11 is a partial cross-sectional assembly view of the adaptor of FIG. 10 attached to a syringe fitting of the present invention.
Figure 11A:
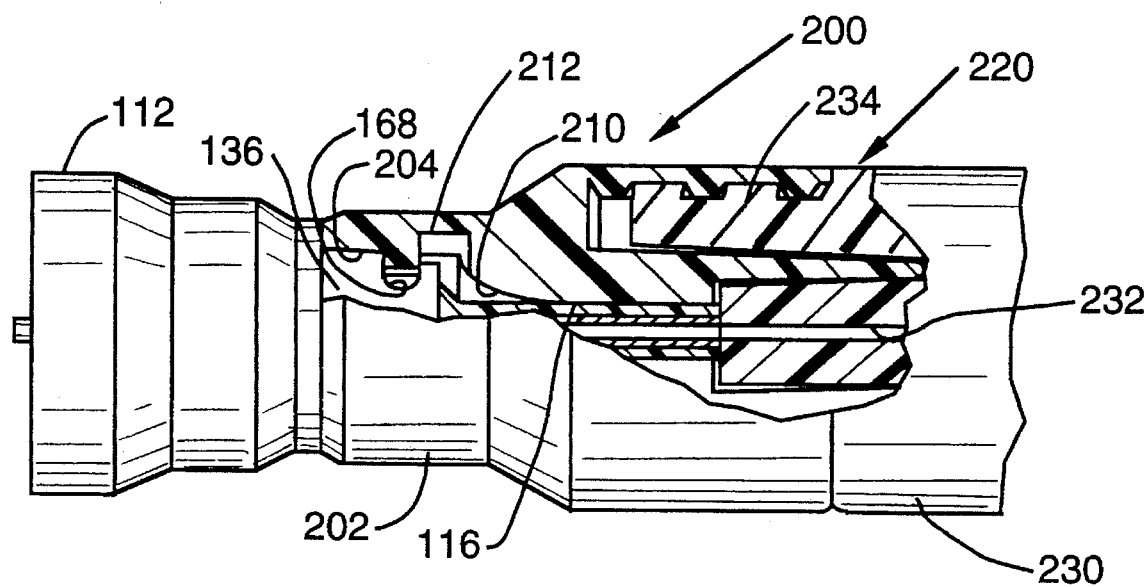
FIG. 11A is a partial cross-sectional assembly view of the adaptor and syringe assembly of FIG. 11 attached to a second ported member.

FIGS. 10 and 11 depict an alternative adaptor 200 that can be used in connection with the fittings 12 or 112. For the purposes of this description, adaptor 200 will be described for use in connection with the fitting 112; however, the skilled artisan will readily appreciate that adaptor 200 can also be attached to fitting 12 in the manner described hereinabove. Adaptor 200, in a preferred form, comprises a luer lock member that has an attachment portion 202 that has a first bore 204 therein that has a taper that corresponds with the taper of the outer surface 137 of the mounting member 136 of a fitting 112. Integrally formed with the attachment portion is a nozzle portion 206. In a preferred embodiment, as shown in FIGS. 10 and 11, the nozzle portion 206 has a counterbore 208 therein that is coaxially aligned with a passageway 210 that is tapered to achieve a sliding fluid-tight fit with the nose 116 of the fitting 112. See FIG. 11.

To secure the adaptor 200 in place upon the fittings 12 or 112, retention means, in the form of a pair of diametrically opposed pins or projections 212 that are formed in the adaptor 200 such that they protrude into bore 204 are provided. The adaptor 200 may be attached to a fitting 112 by aligning the pins 212 with the slot portions 166 of the T-shaped slots 164 in the mounting portion 136 of the fitting 112 and axially inserting the fitting 112 into the bore 204 and tapered passageway 210 in the adaptor 200. After the fitting 112 has been inserted into the adaptor such that the attachment portion 202 of the adaptor 200 is received on the mounting portion 136 as shown in FIG. 11, the adaptor 200 is then rotated clockwise or counterclockwise relative to the fitting 112 such that the pins 212 are no longer in line with the slot portions 166. It will be appreciated that the engagement between the inner surface of bore 204 and the outer surface 137 of the mounting portion 136 of the fitting 112 serve to create a fluid-tight seal between the fitting 112 and the adaptor 200. It will also be appreciated that pins 212 and T-shaped slots mechanically retain the adaptor 200 in such fluid-tight engagement with the fitting 112.

As can be seen in FIGS. 10 and 11, a preferred adaptor 200 also has a locking skirt 220 integrally formed thereon that is coaxially aligned with the nozzle 206. Locking skirt 220 preferably has a series of internal threads 222 formed therein that facilitate the mechanical attachment of the adaptor 200 to a "second" member 230 that has a port 232 and a threaded attachment member 234. See FIG. 11. As can be seen in FIG. 11, a protective cap 240, preferably fabricated from a resilient rubber material, is provided to prevent the nozzle portion 206 from becoming contaminated when it is not connected to a second member 230. Preferably, protective cap 240 is provided with an inwardly protruding seal member 242 that has a conical tip 244 adapted to sealingly engage the end of the tube 138. The skilled artisan will thus appreciate that the protective cap 240 maintains the sterility of the nozzle portion 206 of the adaptor 200 and creates a fluid-tight seal with the adaptor 200 to prevent any leakage of medicament therefrom.

In another preferred embodiment, an adaptor assembly 300 may be employed to enable the syringe 14 to perform subcutaneous injections of medicament received in its fluid carrying body 15. The adaptor assembly 300 preferably comprises a cannula carrier 302 that is preferably fabricated from a resinous material (i.e., polymer or plastic) and is configured as shown in FIGS. 12–15. As will become evident from the following discussion, the cannula carrier 302 can be attached in fluid-tight engagement with the syringe fittings 12 or 112 described above.

Figures 14, 15:
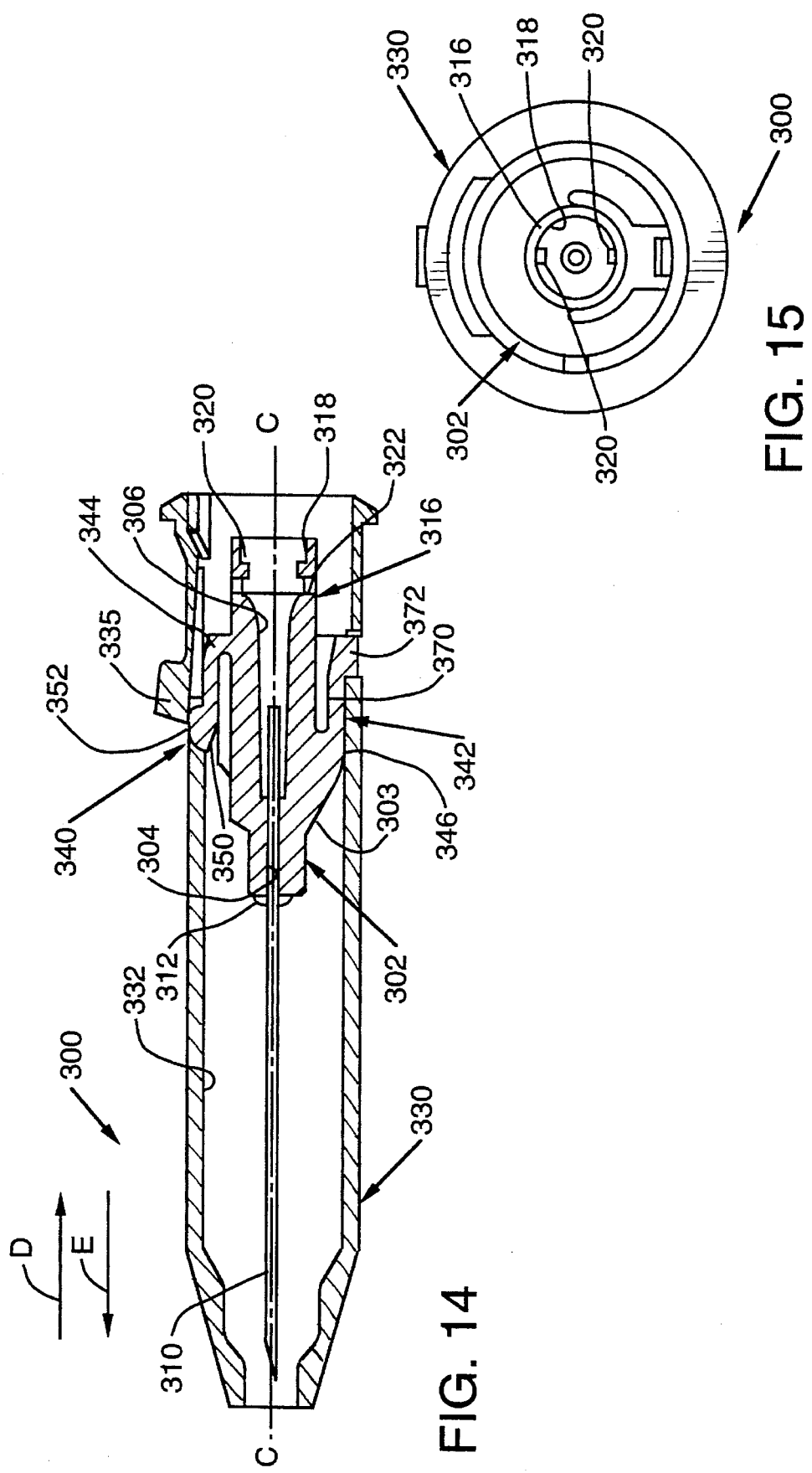
FIG. 14 is a cross-sectional view of the adaptor and sheath assembly depicted in FIGS. 12 and 13.
FIG. 15 is an end view of the adaptor and sheath assembly depicted in FIGS. 12-14.

More specifically and with reference to FIG. 14, the cannula carrier 302 has a body portion 303 that has first axial passageway 304 formed therein that is coaxially arranged on the central axis C—C that passes through the cannula carrier 302. In a preferred embodiment a second tapered passageway 306 is coaxially aligned with the first passageway 304 and is adapted to achieve a close fluid-tight sliding fit with the nose 116 of the fitting 112. It will be appreciated that the taper of the second passageway 306 corresponds with the taper of the nose 116 so as to achieve a fluid-tight seal therebetween when the nose 116 is inserted therein in sliding engagement. The first passageway 304 is sized to slidably receive a cannula 310 member therein. Cannula member 310 is preferably retained within the passageway 304 by an adhesive bond 312 in a manner known in the art which also serves to create a fluid-tight seal between the cannula 310 and the passageway 304. As can be seen in FIG. 14, the cannula 310 preferably extends into the second passageway 306. The skilled artisan will appreciate that the cannula 310 could comprise a hypodermic needle, an intravenous needle, a transfusion needle, a trocar, etc.

To attach the adaptor assembly 300 to either of the fittings 12 or 112, a connection hub 316 is integrally formed on the rear portion of the cannula carrier 302. As can be seen in FIGS. 14 and 15, connection hub 316 has a tapered bore 318 formed therein that is coaxially aligned with the passageways 304 and 306 in the carrier 302. Bore 318 has a taper that corresponds with the taper of the outer surface 137 of the mounting member 136 on the fitting 112. A pair of diametrically opposed pins or projections 320 are integrally formed with the connection hub 316 such that they protrude into the bore 318. The adaptor assembly 300 is attached to a fitting 112 by aligning the pins 320 with the slot portions 166 of the T-shaped slots 164 in the mounting portion 136 of the fitting 112 and axially inserting the fitting 112 into the bore 318 and tapered passageway 306 in the cannula carrier 302. After the fitting 112 has been inserted into the cannula carrier 302 such that the connecting hub 316 of the carrier 302 is received on the mounting portion 136 of the fitting 112, the adaptor assembly 300 is then rotated clockwise or counterclockwise relative to the fitting 112 such that the pins 320 are radially advanced in the slot portions 168 to positions wherein they are no longer in line with the slot portions 166. In a preferred embodiment, to assist in aligning the pins 320 with slot portions 166, a viewing port 322 is provided adjacent each pin 320. See FIG. 14. It will be appreciated that the engagement between the inner surface of bore 318 and the outer surface 137 of the mounting portion 136 of the fitting 112 serve to create a fluid-tight seal between the fitting 112 and connector hub 316. In addition, a fluid-tight seal is created between the second passageway 306 and the nose 116. It will also be appreciated that pins 320 and T-shaped slots 164 mechanically retain the cannula carrier 302 in such fluid-tight engagement with the fitting 112.

Figure 12:
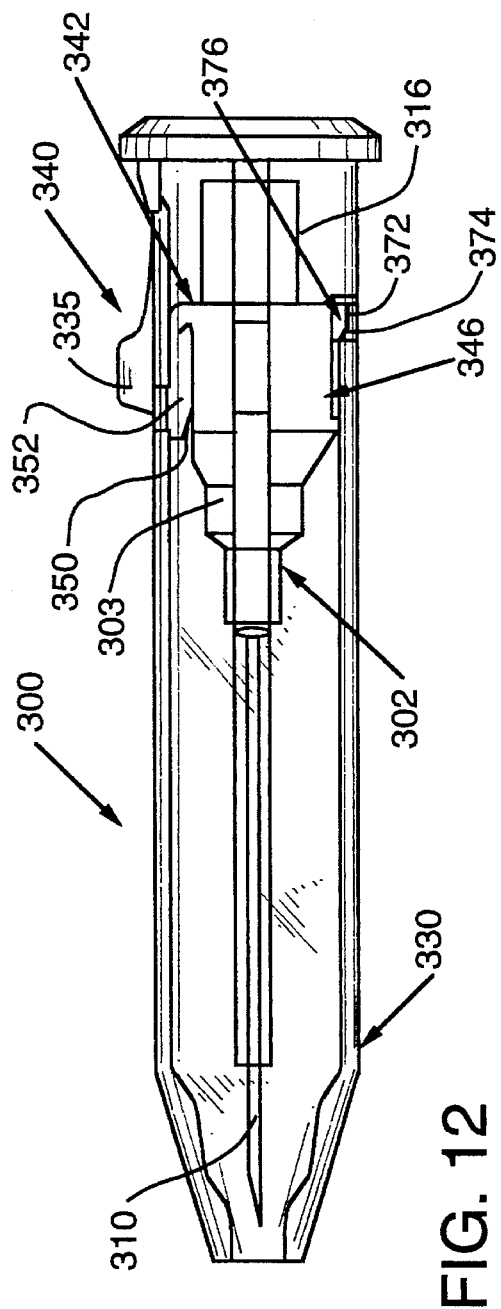
FIG. 12 is an assembly view of yet another adaptor of the subject invention with a preferred protector sheath attached thereto in a first locked position.
Figure 13:
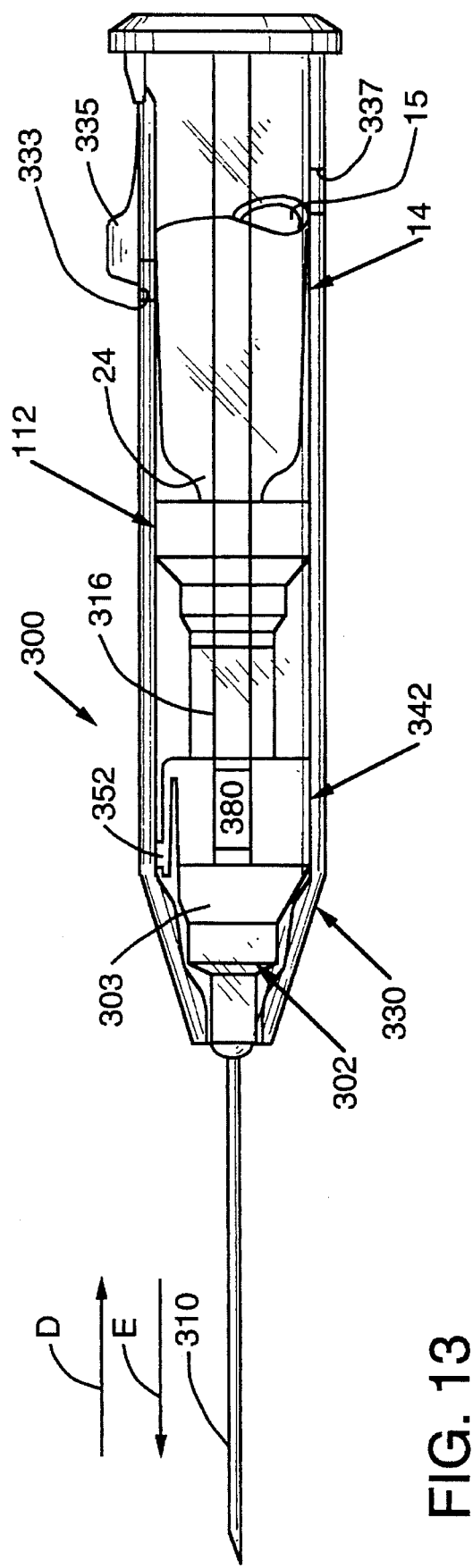
FIG. 13 is an assembly view of the adaptor of FIG. 12 with the protector sheath thereof in a second position.

In a preferred embodiment, the adaptor assembly 300 also includes a protective cannula guard or sheath 330 that can be axially advanced from a first position wherein the cannula 310 is completely housed therein (FIG. 12) and various other positions wherein a portion of the cannula 310 is exposed for injection purposes (FIG. 13). Sheath 330 is preferably fabricated from a transparent plastic material; however, other materials may also be successfully used. As can be seen in FIG. 14, the sheath 330 preferably has an elongated hollow barrel 332 that is sized to slidably receive therein the cannula carrier 302. The barrel 332 is also sized such that when it is axially advanced in the "D" direction relative to the cannula carrier 302, it can slide over the fluid carrying body 15 of the syringe 14. See FIG. 13.

In a preferred embodiment, the sheath 330 is adapted to be selectively locked in the first position by a latch assembly generally designated as 340. As can be seen in FIG. 14, cannula carrier 302 has an outer hub portion 342 integrally formed thereon that extends around the body portion 303. A first portion 344 of the hub 342 is spaced away from the body portion 303 as shown in FIG. 14. A first cantilever latch member 350 is formed into the first portion 344 of the hub 342 such that it can be selectively displaced into the space between first portion 344 and the body portion 303. The first latch member 350 preferably has a latch tab 352 formed thereon that is adapted to be received in a corresponding latch cavity 333 provided in the sheath 330. See FIG. 13. As can be seen in FIGS. 12–14, a cantilevered disengagement tab 335 is formed in the sheath 330 such that it can be selectively displaced into contact with the latch tab 352 to bias it out of the latch cavity 333. Thus, when the sheath 330 is in the first position as shown in FIG. 12, the latch tab 352 is received in the latch cavity 333 to thereby retain the sheath 330 in that locked position. To release the sheath 330, the disengagement tab 335 is pressed into contact with the latch tab 352 to bias it out the latch cavity 333 thereby permitting the sheath 330 to be axially advanced on the cannula carrier 302.

Also in a preferred embodiment, the adaptor assembly 300 is preferably provided with means for preventing the sheath 330 from being accidentally separated from the cannula carrier 302. More specifically, as can be seen in FIGS. 12 and 14, the hub 342 has a second portion 346 that extends around the body portion 303 of the cannula carrier 302 in a spaced-apart relationship. A cantilevered retaining catch 370 is formed in the second portion 346 of the hub 342 such that it can be selectively displaced into the space between the second hub portion 346 and the body portion 303. A retaining tab 372 is formed on the catch and is adapted to be received in a corresponding cavity 337 in the sheath 330. As can be seen in FIG. 12, the forward surface 374 of the retaining tab 372 is angled slightly such that when the sheath 330 is axially advanced in the "D" direction relative to the carrier 302, the forward surface 374 will cam out of engagement with the cavity 337. However, the rear surface 376 of the retaining tab 372 is perpendicular to the direction of axial travel and thus engages the rear wall of the cavity 337 when the sheath 330 is axially advanced in the "D" direction to thereby prevent the sheath from being accidentally separated from the cannula carrier 302. It will be appreciated that the tapered forward portion of the sheath is sized to engage the carrier to prevent it from being separated therefrom when the sheath is moved in the "E" direction. See FIG. 12.

Also in a preferred embodiment, to keep the latch member 350 aligned with cavity 333 and retaining catch 370 aligned with cavity 337, a key 380 is formed on the cannula carrier 302. Key 380 is adapted to be slidably received in an axially extending keyway 339 provided in the sheath 330. It will be appreciated that such key and keyway arrangement prevents the sheath 330 from being rotated relative to the cannula carrier and thus maintains retaining catch 370 axially aligned with cavity 337 and latch member 350 axially aligned with cavity 333.

Figure 16:
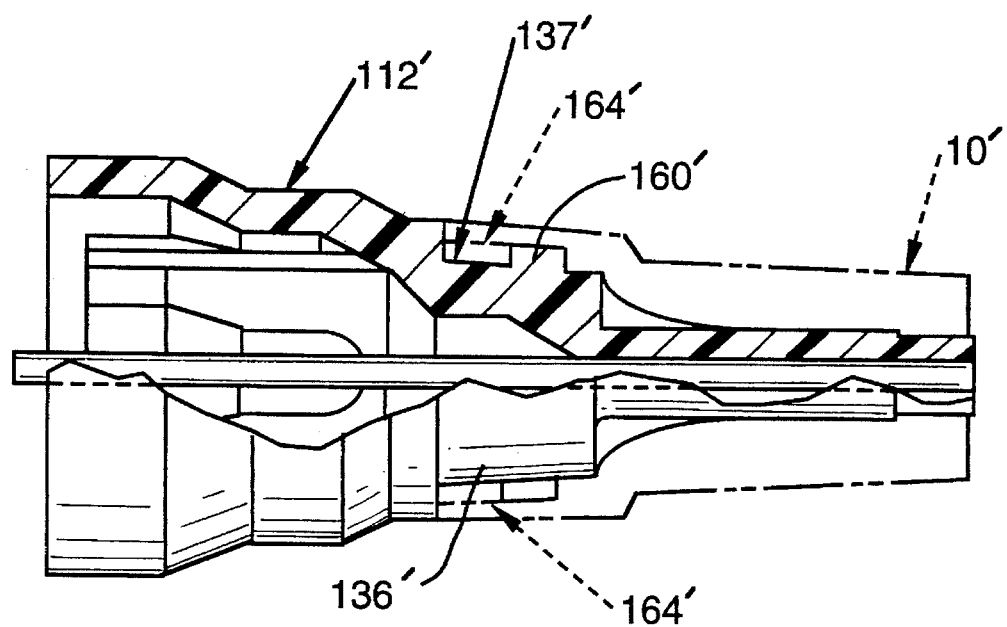
FIG. 16 is a partial cross-sectional assembly view of another syringe fitting and adaptor of the present invention.

The skilled artisan will also readily appreciate that the adaptor system embodiments described above may be alternatively constructed such that the retaining slots are provided in the adaptor member and the pins are formed such that they protrude from the outer perimeter of the mounting portion of the fitting. For example, as shown in FIG. 16, pins 160' are formed on the surface 137' of the mounting member 136' of a fitting 112' and are adapted to engage T-slots 164' provided in the adaptor 10'. The construction of the fitting 112' and the adaptor 10' are otherwise the same as the construction of fitting 112 and adaptor 10, respectively. Those of ordinary skill in the art will also appreciate that the above described adaptor systems may employ a single retaining pin 60 or 60' or, if desired, more than two of such pins may be employed for retaining an adaptor in engagement with a corresponding syringe fitting.

As can be gleaned from the description recited above, the present invention provides a number of solutions to problems that have been encountered when using other known syringe and adaptor arrangements. In particular, the present invention enables a syringe to selectively interface with different I.V. or other port configurations. The present invention also enables a syringe to be selectively used in connection with an I.V. port arrangement or used to perform subcutaneous injections of medicament. The subject invention also provides a unique and novel adaptor arrangement that enables an adaptor to be quickly attached to a syringe fitting and be rotatably manipulated relative to the fitting without compromising the fluid-tight seal therebetween. It will be understood, however, that various changes in details, materials and arrangements of parts which have been herein described and illustrated in order to explain the nature of the invention may be made by those skilled in the art within the principle and scope of the invention as expressed in the appended claims.

What is claimed is:

1. An adaptor system for use in connection with a syringe having a fluid carrying body, the system comprising:

a syringe fitting having a hollow element protruding therefrom and being attachable to said syringe such that said hollow element is in fluid communication with said fluid carrying body;

an adaptor member having a port therein, said port having an interior surface configured for fluid-tight engagement with the outer surface of said hollow element; and means for retaining said hollow element in fluid-tight engagement with said adaptor port, said retaining means comprising at least one protrusion on said adaptor member and a T-shaped slot in said syringe fitting corresponding to each said protrusion such that when said protrusions are simultaneously aligned with their corresponding T-shaped slot, said hollow element may be axially inserted into said adaptor port to establish said fluid-tight seal therewith and be selectively rotated in two radial directions relative to said syringe fitting while maintaining said fluid-tight seal therebetween.

2. The adaptor of claim 1 wherein at least a portion of said outer surface of said hollow element and at least a portion of the interior surface of said adaptor port are each tapered such that when said hollow element is axially inserted into said adaptor port, said fluid-tight seal is established therebetween.

3. The adaptor system of claim 2 wherein said tapered portion of said hollow element and said tapered portion of said interior surface of said adaptor port are each tapered within the range of 1.5–2.0 degrees.

4. The adaptor system of claim 1 wherein said syringe fitting has an axial bore therethrough and a metal tube disposed within said axial bore to define a hollow passage through said syringe fitting to facilitate said fluid communication with said fluid carrying body.

5. The adaptor system of claim 1 wherein said protrusions are formed in said outer surface of said hollow element and wherein said corresponding T-shaped slots are formed in the interior surface of said adaptor port.

6. The adaptor system of claim. 1 wherein said adaptor member has a nozzle portion that has a passageway extending therethrough that is sized to receive a portion of said hollow element for fluid-tight engagement therewith, said nozzle protruding from said adaptor member and having a configuration that differs from the configuration of said hollow element for insertion into a corresponding second port in a second member.

7. The adaptor system of claim 6 wherein at least one rib is formed on the exterior of said adaptor member to facilitate the manual manipulation of said adaptor member relative to said syringe fitting.

8. The adaptor system of claim 6 wherein said adaptor member further includes attachment means for removably attaching said adaptor member to said second member.

9. The adaptor system of claim 8 wherein said attachment means comprises threads formed on said adaptor member for engagement with a corresponding portion of said second member.

10. The adaptor system of claim 6 further comprising a closure member removably attachable to said adaptor member to create a substantially fluid-tight seal with said nozzle portion thereof.

11. The adaptor system of claim 1 wherein said adaptor member has a needle operably attached thereto such that said needle is in fluid communication with said fluid carrying body of said syringe fitting when said adaptor is attached thereto.

12. The adaptor system of claim 11 further comprising a protective sheath attached to said adaptor member and being selectively axially displaceable on said adaptor member between a first axial position wherein said needle is completely housed within said sheath and other positions where a portion of said needle is exposed.

13. The adaptor system of claim 12 further comprising means for selectively retaining said sheath in said first axial position.

14. The adaptor system of claim 13 further comprising means attached to said adaptor member for preventing said sheath from being detached therefrom.

15. The adaptor system of claim 11 further comprising a viewing aperture in said adaptor adjacent to at least one said protrusion to provide a means for visually determining the position of said adjacent protrusion relative to said corresponding T-shaped slot to enable said adjacent protrusion to be aligned with said corresponding T-shaped slot in said syringe fitting.

* * * * *